United States Patent [19]
Peterson et al.

[11] 3,987,191
[45] Oct. 19, 1976

[54] (ORGANOSULFINYLMETHYL)TRI-ORGANOTIN ACARICIDAL COMPOSITIONS AND METHODS OF USE

[75] Inventors: Donald J. Peterson, Cincinnati; James F. Ward, Fairfield, both of Ohio

[73] Assignee: The Procter & Gamble Company, Cincinnati, Ohio

[22] Filed: July 29, 1974

[21] Appl. No.: 492,383

Related U.S. Application Data
[62] Division of Ser. No. 339,449, March 8, 1973, Pat. No. 3,850,970.

[52] U.S. Cl. .................... 424/288; 71/97
[51] Int. Cl.² ......................... A01N 9/00
[58] Field of Search ............ 71/97; 424/288

[56] References Cited
UNITED STATES PATENTS

| | | | |
|---|---|---|---|
| 3,095,434 | 6/1963 | Stamm et al. | 260/429.7 |
| 3,538,088 | 11/1970 | Hartman | 260/429.7 |
| 3,725,446 | 4/1973 | Peterson | 260/429.7 |
| 3,784,580 | 1/1974 | Peterson | 260/429.7 |
| 3,794,670 | 2/1974 | Peterson | 260/429.7 |
| 3,808,264 | 4/1974 | Peterson | 260/429.7 |

*Primary Examiner*—V. D. Turner
*Attorney, Agent, or Firm*—Rose Ann Dabek; Jerry J. Yetter; Richard C. Witte

[57] ABSTRACT

Disclosed are novel(organosulfinylmethyl) triorganotin compounds and a process for preparing same. These organotin compounds correspond to the general formula:

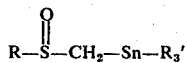

where R is a 1 to 14 carbon atom alkyl, aryl or substituted aryl group and each R' is an alkyl group of 1 to 10 carbon atoms. The organotin compounds of the invention have insecticidal, acaricidal and herbicidal properties and are employed in the formulation of pesticidal compositions effective for combating these pests.

10 Claims, No Drawings

(ORGANOSULFINYLMETHYL)TRI-ORGANOTIN ACARICIDAL COMPOSITIONS AND METHODS OF USE

This is a division of application Ser. No. 339,449, filed Mar. 8, 1973, now U.S. Pat. No. 3,850,970 granted Nov. 26, 1974 to Donald J. Peterson and James F. Ward.

BACKGROUND OF THE INVENTION

This invention relates to novel compounds. More particularly, this invention relates to novel (organosulfinylmethyl) triorganotin compounds, a method for their preparation, pesticidal compositions containing such compounds and to a method of combating pests.

The desirability of controlling or eradicating various insects and weeds is clearly accepted. Thus, compounds possessing insecticidal, acaricidal, and herbicidal properties and especially adapted to such control or eradication are of particular importance.

It is an object of the present invention to provide novel organotin compounds and a method for their preparation.

A further object is to provide novel compounds which are useful as pesticides. Another object is to provide pesticidal compositions containing the novel organotin compounds. A still further object is to provide novel compositions and methods effective for combating pests. Other objects of the invention will be apparent from consideration of the invention described more fully hereinafter.

DETAILED DESCRIPTION OF THE INVENTION

The novel (organosulfinylmethyl) triogranotin compounds of the present invention have the formula:

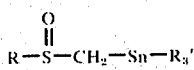

where R is a member selected from the group consisting of 1 to 14 carbon atom alkyl, aryl and substituted aryl radicals wherein in the substituted aryl radicals the substituents are selected from the group consisting of $C_1$ to $C_4$ alkyl, $C_1$–$C_4$ alkoxy, halogen, and nitro, and wherein R′ is alkyl containing from 1 to about 10 carbon atoms. Preferably R is methyl or phenyl and R′ is $C_4$ to $C_6$ straight chain alkyl. When R′ is $C_4$ to $C_6$ alkyl, the compounds have been found to be optimum with respect to high pesticidal activity and low mammalian toxicity. Examples of compounds of the invention are: (methyl-sulfinylmethyl) triethyltin, (methylsulfinylmethyl) tri-n-butyltin, (methylsulfinylmethyl) tri-n-hexyltin, (n-hexylsulfinylmethyl) tri-n-hexyltin, (n-dodecylsulfinylmethyl) tri-n-butylin, (2-naphthylsulfinylmethyl) tri-n-butyltin, (phenylsulfinylmethyl) tri-n-butyltin, (4-chlorophenylsulfinylmethyl) tri-isopropyltin, (4-bromo-2-naphthylsulfinylmethyl) tri-n-butyltin, (4-methyl-2-naphthylsulfinylmethyl) tri-n-hexyltin, (4-nitrophenylsulfinylmethyl) tri-n-butyltin and (2-ethoxyphenylsulfinylmethyl) tri-n-butyltin. The R′ groups on the tin can also be mixed as for example in (methylsulfinylmethyl) methyl diethyltin. Preferred compounds are (methylsulfinylmethyl) tri-n-butyltin, (methylsulfinylmethyl) tri-n-hexyltin, (phenylsulfinylmethyl) tri-n-butyltin and (phenylsulfinylmethyl) tri-n-hexyltin.

In its process aspect, the invention provides a method of preparing the novel (organosulfinylmethyl) triorganotin compounds, comprising the steps of:

1. admixing a triorganotin amine compound of the formula $(R'_3Sn)_xNR''_{3-x}$ wherein $x$ is an integer from 1 to 3 and where R′ is as defined above and R″ is as defined hereinafter, with a methyl sulfoxide of the formula $RS(O)CH_3$, wherein R is as defined above, and
2. heating the mixture from Step (1) at a temperature of from about 25° C to 125° C, and recovering the (organosulfinylmethyl) triorganotin compound.

The reaction can be described graphically as follows:

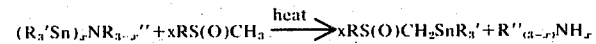

wherein $x$ is an integer from 1 to 3, wherein R and R′ are defined as above and wherein R″ is $C_1$–$C_6$ alkyl, cycloalkyl, or hydrogen.

The organotin amimes used as reactants in the above reaction can be prepared by reacting the alkali metal salts of ammonia and primary and secondary amines with triorganotin halides, e.g. triorganotin fluorides, chlorides, bromides and iodides, which are commercially available. The alkali metal salts of primary and secondary amines and ammonia are themselves prepared by reacting said amines or ammonia with the corresponding metals in the manner well-known to those skilled in the art. For example, ammonia will react with sodium to yield sodamide, which, in turn will react with a triorganotin halide to prepare the corresponding triorganotin amine. Dimethylamine will react with lithium metal in the presence of a conjugated diene such as butadiene to form lithium dimethylamide, which, in turn, reacts with a triorganotin halide to form the (N,N-dimethylamino) triorganotin compound. Alternatively, various amines can be metalated in standard fashion with, for example, organolithium compounds to provide the metal amides. In general terms, the preparation of the triorganotin amines useful herein is represented by the following reaction sequence

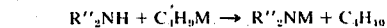
or,
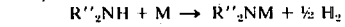
then,
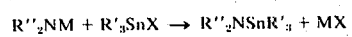

where M is alkali metal, i.e. lithium, sodium, potassium rubidium and cesium; wherein R″ and R′ are as defined above and X is halide, i.e. fluoride, chloride, bromide or iodide. It will be recognized that when primary amines and ammonia are used, varying ratios of triorganotin amines of the formula $(R'_3Sn)_2NR''$ and $R'_3SnHNR''$, and $(R'_3Sn)_3N$, $(R_3Sn)_2NH$ and $R_3SnNH_2$ respectively, are formed. These are all useful in preparing the (organosulfinylmethyl)triorganotin compounds of the present invention.

For economic reasons, sodium is the preferred alkali metal for use in preparing the alkali metal salts of the amines. Ammonia or any amine having at least one N–H bond capable of reacting with a metalating agent to form an alkali metal amine salt is suitable for preparing the triorganotin amines used herein. Generally, however ammonia and alkyl amines containing from 1 to 6 carbon atoms, and preferably 1 to 4 carbon atoms, are preferred. Exemplary amines used in this procedure include methylamine, dimethylamine, ethylamine, diethylamine and ammonia. Especially preferred herein are ammonia, methylamine, dimethylamine, ethylamine and diethylamine. This is for economic reasons and also because these amines, when liberated during the reaction between the triorganotin amine and the sulfoxide, are easily removed by distillation from the reaction medium due to their relatively high volatility. The triorganotin halides suitable for preparing the triorganotin amines used herein are commercially available. Such compounds are prepared, for example, by reacting an organometallic compound with a tin tetrahalide in the manner well-known to those skilled in the art. Exemplary triorganotin halides suitable for preparing the triorganotin amines used in the present process include trimethyltin chloride, triethyltin bromide, tripropyltin fluoride, tributyltin chloride, trisdecyltin chloride and the like. The trialkyl tin chlorides are preferred for economic reasons.

From the foregoing it may be seen that a variety of trialkyltin amines useful in the present process can be readily prepared using standard techniques. To facilitate ease of removal of the liberated amine in the reaction of the trialkyl tin amine with the sulfoxide it is generally preferred that the R'' groups on the trialkyltin amine be hydrogen, methyl or ethyl. Preferred trialkyltin amines used in the process of the present invention are the bis(trialkyltin) amines [$(R'_3Sn)_2NH$], tris(trialkyltin) amines [$R'_3Sn)_3N$], bis (trialkyltin)-N-methylamines [$(R'_3Sn)_2NCH_3$], aminotrialkyltins [$R'_3SnNH_2$], N-methylaminotrialkyltins [$R'_3SnNHCH_3$] and N,N-dimethylaminotrialkyltins [$R'_3SnN(CH_3)_2$]. Of these, the compounds wherein R' is straight chain $C_4$ to $C_6$ alkyl are preferred. When ease of preparation and handling are of primary concern, N,N-diethyl $C_4$–$C_6$ straight chain alkyl tin or N,N-dimethyl $C_4$–$C_6$ straight chain alkyl tin are preferably used.

The methyl sulfoxides used in the process herein have the formula $RS(O)CH_3$ wherein R is $C_1$ to $C_{20}$ alkyl, aryl or substituted aryl wherein the aryl substitutents are selected from the group consisting of halogen, nitro, $C_1$ to $C_4$ alkyl and $C_1$ to $C_4$ alkoxy. Such methyl sulfoxides are commercially available or, alternatively they can be prepared in wellknown fashion by the controlled oxidation of the corresponding sulfides of the formula $RSCH_3$, using for example, hydrogen peroxide in glacial acetic acid, sodium hypochlorite, or potassium permanganate at elevated temperatures, as oxidizing agents. Examples of sulfoxides for use in the present process are: dimethyl sulfoxide, n-butyl methyl sulfoxide, n-octyl methyl sulfoxide, phenyl methyl sulfoxide, 2-naphthyl methyl sulfoxide, 4-chlorophenyl methyl sulfoxide, 4-bromo-2-naphthyl methyl sulfoxide, 4-nitrophenyl methyl sulfoxide, 4-ethylphenyl methyl sulfoxide, 3-methoxyphenyl methyl sulfoxide and 4-ethoxyphenyl methyl sulfoxide. Expecially preferred are dimethyl sulfoxide and phenyl methyl sulfoxide.

The process herein is generally carried out by admixing the triorganotin amine with the sulfoxide at a molar equivalent ratio of from about 1:100 to 100:1, preferably, about 1:1; conducting the reaction at a temperature from about 25° C to 125° C for a period from about 1 to about 24 hours; and recovering the desired (organosulfinylmethyl) triorganotin compound by crystallization, chromatography or distillation, depending on the physical form of the compound being prepared. For example, liquid (organosulfinylmethyl) triorganotin compounds are generally recovered by distillation while the solid (organosulfinylmethyl) triorganotin compounds are readily recovered by column chromatography or crystallization. Preferably, in order to improve the degree of reaction completion, the free amine which is formed during the reaction is continuously removed by distillation.

While the process of this invention is preferably carried out in the absence of solvent, it is sometimes convenient to use a solvent or suspending liquid herein. Any of the common organic solvents can be used for this purpose, including for example, hexane, benzene, toluene xylene, and the like. Mixtures such as the petroleum ethers and the glyme solvents are also suitable. If a solvent is used, its boiling point should preferably exceed that of the liberated amine so that the amine can be continuously removed by distillation. Preferred solvents are anhydrous aprotic organic liquids, especially xylene. Sufficient solvent is used to dissolve or disperse the reactants.

The reaction temperature in this process should be at least 25° C to ensure a reasonable reaction rate, but should not exceed 125° C since side reactions and decompositon of the principal reaction product tend to occur at temperatures above about 125° C. Preferably the reaction temperature should be from about 50° to 100° C. The reaction is initiated almost immediately upon mixing, and the reaction time employed will vary with temperature, the amount of tin amine being reacted with the sulfoxide, and the like. Usually, from about 10 minutes to 24 hours is sufficient.

The novel compounds of the present invention are useful for destroying a variety of pests, particularly insects, mites and weeds. Accordingly, a method aspect of the present invention comprises combatting pests by applying to said pests or their habitat a pesticidally effective amount of one or more of the novel compounds of the invention. The required dosage depends upon many factors such as method of application, type and degree of pest infestation, frequency of treatment, climatic conditions, etc. In agricultural use (i.e. on field crops) application rates of about 0.5 to 50 lbs. of organotin compound per acre are usually satisfactory, but higher rates can also be used. Preferably the application rate is about 1 to 30 lbs. per acre.

For practical use as pesticides, the organotin compounds of the invention are generally incorporated into pesticidal compositions which comprise an inert carrier and a pesticidally effective amount of one or more of the organotin compounds. (As used herein an inert carrier is defined as a solvent or a dry bulking agent which has substantially no pesticidal effectiveness but which provides a means whereby the organotin compounds are diluted for convenient application.) Such compositions enable the organotin compounds to be applied conveniently to pests or their habitats in any desired quantity. These compositions can be solids, such as dusts, granules or wettable powders, or they can be liquids such as solutions, aerosols, or emulsifiable concentrates. The solid compositions generally contain from about 0.5% to about 95% by weight of the organotin compounds and the liquid compositions generally contain from about 0.5 to about 70% by weight of said compounds.

Dusts can be prepared by grinding and blending the organotin compounds with a solid carrier such as talcs, clays, silicas, pyrophylite and the like. Granular formulations can be prepared by impregnating the organotin compounds, usually dissolved in a suitable solvent, onto and into granulated carriers such as the attapulgites or the vermiculites, usually of a particle size range of from about 0.3 to 1.5 mm, or by coating an inert carrier with a wettable powder formulation of the compounds. Wettable powders, which can be dispersed in water or oil to any desired concentration of the organotin compounds, can be prepared by incorporating wetting agents into concentrated dust compositions.

Preferred pesticidal compositions for the practice of the invention herein are emulsifiable concentrates which comprise the organotin compound, and, as an inert carrier, an emulsifier and an organic solvent. Such concentrates can be extended with water and/or additional organic solvent to any desired concentration of the organotin compound for application as sprays to the site of pest infestation. The emulsifiers used in these concentrates are surface active agents of the anionic, nonionic, cationic, ampholytic or zwitterionic type and normally comprise from about 0.1% to 30% by weight of the concentrate. Examples of suitable anionic surface active agents are sodium salts of fatty alcohol sulfates having from 8-18 carbon atoms in the fatty chain and sodium salts of alkyl benzene sulfonates, having from 9 to 15 carbon atoms in the alkyl chain. Examples of suitable nonionic surface active agents are the polyethylene oxide condensates of alkyl phenols, wherein the alkyl chain contains from about 6 to 12 carbon atoms and the amount of ethylene oxide condensed onto each mole of alkyl phenol is from about 5 to 25 moles. Examples of suitable cationic surface active agents are dimethyl dialkyl quaternary ammonium salts wherein the alkyl chains contain from about 8 to 18 carbon atoms and the salt forming anion is a halogen. Examples of suitable ampholytic surface active agents are derivatives of aliphatic secondary or tertiary amines in which one of the aliphatic substituents contains from about 8 to 18 carbon atoms and one contains an anionic water solubilizing group, e.g. sulfate or sulfo. Specific suitable ampholytic surface active agents are sodium-3-dodecylaminopropionate and sodium-3-dodecylaminopropane-1-sulfonate. Examples of suitable zwitterionic surface active agents are derivatives of aliphatic quaternary ammonium compounds in which one of the aliphatic constituents contains from about 8 to 18 carbon atoms and one contains an anionic water solubilizing group. Specific examples of zwitterionic surface active agents are 3-(N,N-dimethyl-N-hexadecylammonio) propane-1-sulfonate and 3-(N,N-dimethyl-N-hexadecylammonio)-2-hydroxy propane-1-sulfonate. Many other suitable surface active agents are described in Detergents and Emulsifiers - 1972 Annual by John W. McCutcheon Inc. which is incorporated by reference herein. Suitable solvents for these emulsifiable concentrates include hydrocarbons such as benzene, toluene, xylene, kerosene and Stoddard Solvent and halogenated hydrocarbons such as chlorobenzene, chloroform, fluorotrichloromethane and dichlorodifluoromethane. Typical liquid concentrates comprise from about 0.5% to 70% organotin compound, from about 0.1% to 30% emulsifier and from about 29.9% to about 99.4% organic solvent.

The following examples are included herein to more fully illustrate the present invention but are not intended to be limiting thereof.

EXAMPLE I

Preparation of (Phenylsulfinylmethyl) Tributyltin

Phenyl methyl sulfoxide (7.0 g.; 0.05 moles) and dimethylamino tributyltin (16.7 g.; 0.05 moles) were admixed in a 50 ml round bottom flask, under a positive pressure argon atmosphere, for 20 hours at 100° C. During the reaction, liberated dimethylamine gas exited from the reaction flask through an open port with the moving argon gas. The crude product was distilled through a semi-micro distillation apparatus. The main fraction (13 g; 65% yield) distilled at 160°–170° C at 0.05 mm Hg. The product was identified by $^1$H NMR and infra red spectra as (phenylsulfinylmethyl) tributyltin.

EXAMPLE II

Preparation of (Methylsulfinylmethyl) Tributyltin

Dimethylamino tributyltin (33.4 g.; 0.1 moles) and dimethylsulfoxide (100 g.; 1.28 moles) were stirred in a 250 ml reaction flask, under a positive pressure argon atmosphere, for 4.5 hours at 80° C. During the reaction, liberated dimethylamine gas exited from the reaction flask through an open port with the moving argon gas. The reaction stood overnight at ambient temperature. Excess dimethylsulfoxide was distilled at 75° C at 15 mm Hg. The reaction product was distilled through a semi-micro distillation apparatus at 138° C at 0.1 mm Hg. Yield of 25 g (68%) was identified as (methylsulfinylmethyl) tributyltin by $^1$H NMR and infrared spectra.

EXAMPLE III

Compounds of the invention were tested for herbicidal effectiveness according to the following procedure.

a. Preparation and application of materials

The desired amount of compound was dissolved in acetone, containing 500 ppm of Span 85 (sorbitan trioleate emulsifier) and Tween 80 (polyoxyethylene sorbitan monooleate emulsifier). The formulations are applied with a Devilbiss atomizer operating at 6 p.s.i. pressure and delivering 50 ml. of formulation on both pre-emergence and post emergence pots.

b. Pre-emergence tests

Duplicate paper pots filled with a soil mixture are seeded at a depth of one-half inch with mustard, pigweed crabgrass and foxtail. Immediately after seeding, the soil is sprayed with the solution. Growth is allowed to occur under artificial light with overhead irrigation. The plants are observed for about 10 days and an injury rating is given in comparison with untreated controls.

c. Post-emergence tests

Duplicate paper pots filled with vermiculite are seeded at a depth of one-half inch with the same plants employed in the pre-emergence tests.

Growth occurs under artificial light with irrigation provided by placing the porous pots in a small amount of water in stainless steel trays. After about 10 days, when the plants reach a suitable size, they are sprayed with the formulation. Observations are made for 10 days and an injury rating is given in comparison with untreated controls.

Results obtained in these tests are shown in Table 1.

TABLE 1

| Treatment | | Mustard | | Pigweed | | Crabgrass | | Foxtail | |
|---|---|---|---|---|---|---|---|---|---|
| | | Pre | Post | Pre | Post | Pre | Post | Pre | Post |
| $CH_3S(O)CH_2Sn(C_4H_9)_3$ | 5 lbs./acre | 5* | — | 5 | — | 4 | — | 4 | — |
| Same | 2 lbs./acre | — | 5 | — | 5 | — | 4 | — | 3 |
| $C_6H_5S(O)CH_2Sn(C_4H_9)_3$ | 5 lbs./acre | 5 | — | 5 | — | 4 | — | 4 | — |
| Same | 2 lbs./acre | — | 5 | — | 5 | — | 4 | — | 3 |

*Plant injury rated on a 0(no injury) to 5(death) scale.

EXAMPLE IV

Compounds of the invention were tested for insecticidal effectiveness against adult house flies, southern armyworm larvae, Mexican bean beetle larvae and pea aphids in the following manner. The compounds are dissolved in acetone and dispersed in distilled water with emulsifiers. The emulsifiers in these aqueous dispersions were 100 ppm Span 85 (sorbitan trioleate) and 20 ppm Tween 80 (polyoxyethylene sorbitan monooleate). The compositions are applied for a ten-second period to insects retained in a 2×5 inch diameter screened cage. The spray is applied from a Water's vertical spray tower operating at 10 p.s.i. pressure and discharging about 30 ml. per minute through an atomizer. The spray descends through an 8 inch stainless steel cylinder to the insects below the atomizer. The insects are retained in the sprayed cages for mortality observations. In the case of house fly treatment, two hour data represent knockdown, 24 hour data refer to mortality. The results are set forth in Table 2.

TABLE 2

| TREATMENT | Conc. % w/v | Houseflies 2 hr. | Houseflies 24 hr. | Sou. Armyworms 48 hrs. | Mex. B. Beetles 48 hrs. | Pea Aphids 48 hrs. |
|---|---|---|---|---|---|---|
| $CH_3S(O)CH_2Sn(C_4H_9)_3$ | 0.1 | 78 | 18 | 100 | 90 | 100 |
| | 0.05 | — | — | 70 | 60 | 100 |
| | 0.01 | — | — | 60 | 30 | 0 |
| $C_6H_5S(O)CH_2Sn(C_4H_9)_3$ | 0.1 | 30 | 4 | 100 | 50 | 100 |
| | 0.05 | — | — | 80 | — | 100 |
| | 0.01 | — | — | 50 | — | 0 |

The figures indicate percent of insects killed.

EXAMPLE V

Compounds of the invention were tested for miticidal effectiveness against strawberry spider mites in the following manner. The test compositions are prepared in the same manner as in EXAMPLE IV. Bean seedlings are infested with approximately one hundred mites each. The test compositions are sprayed onto the infested seedlings. After 5 days the plants are examined both for post-embryonic forms of mites and for eggs. The percentage of kill is determined on the basis of the original number of mites subjected to the test treatment. The miticidal results are reported in Table 3.

TABLE 3

| TREATMENT | Conc. % w/v | % Mortality (5 days) |
|---|---|---|
| $CH_3S(O)CH_2Sn(C_4H_9)_3$ | 0.1 | 100 |
| | 0.05 | 100 |
| | 0.01 | 100 |
| | 0.005 | 96 |
| | 0.001 | 30 |
| $C_6H_5S(O)CH_2Sn(C_4H_9)_3$ | 0.1 | 100 |
| | 0.05 | 100 |
| | 0.01 | 74 |
| | 0.005 | 95 |
| | 0.001 | 54 |

EXAMPLE VI

A concentrated composition of the invention is prepared by mixing the following ingredients

| | % by weight |
|---|---|
| (Methylsulfinylmethyl)tri-n-butyltin | 25 |
| Nonionic emulsifier* | 5 |
| Xylene | 70 |
| | 100 |

*Condensation product of nonylphenol with 15 moles of ethylene oxide.

The concentrate is a stable homogeneous liquid. When diluted with 100 parts of water per 1 part of concentrate it forms a stable oil-in-water emulsion which is suitable for spraying onto areas of insect and weed infestation.

What is claimed is:

1. An acaricidal composition comprising from about 0.5% to 95% of an (organosulfinylmethyl) triorganotin compound having the formula

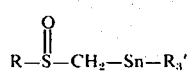

wherein R is $C_1$ to $C_{14}$ alkyl, aryl or substituted aryl wherein the aryl substituents are selected from the group consisting of $C_1$ to $C_4$ alkyl, $C_1$ to $C_4$ alkoxy, halogen and nitro, and R' is $C_1$ to $C_{10}$ alkyl and from about 5% to about 99.5% of an inert carrier.

2. The composition of claim 1, wherein the composition is in the form of a liquid concentrate comprising from about 0.5 to 70% by weight of the (organosulfinylmethyl) triorganotin compound, from about 0.1% to about 30% by weight of an emulsifier and from about 29.9% to about 99.4% of an organic solvent.

3. The composition of claim 2 wherein the R in the (organosulfinylmethyl) triorganotin compound is selected from the group consisting of methyl and phenyl, and the R' is $C_4$ to $C_6$ alkyl.

4. A method for controlling acarid infestation comprising the application to said acarid or habitat thereof an acaricidally effective amount of a compound having the formula

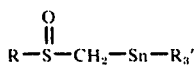

wherein R is selected from the group consisting of $C_1$ to $C_{14}$ alkyl, aryl or substituted aryl groups wherein the aryl substitutents are selected from the group consisting of $C_1$ to $C_4$ alkyl, $C_1$ to $C_4$ alkoxy, halogen and nitro, and R' is $C_1$ to $C_{10}$ alkyl.

5. The method of claim 4, wherein R is selected from the group consisting of methyl and phenyl.

6. The method of claim 5 wherein R' is selected from the group consisting of $C_4$ to $C_6$ alkyls and mixtures thereof.

7. The method of claim 6 wherein the compound is (methylsulfinylmethyl) tri-n-butyltin.

8. The method of claim 6 wherein the compound is (methylsulfinylmethyl) tri-n-hexyltin.

9. The method of claim 6 wherein the compound is (phenylsulfinylmethyl) tri-n-butyltin.

10. The method of claim 6 wherein the compound is (phenylsulfinylmethyl) tri-n-hexyltin.

* * * * *